(12) United States Patent
Jones et al.

(10) Patent No.: US 9,029,761 B2
(45) Date of Patent: May 12, 2015

(54) METHODS FOR ANALYZING SUBSTANCES CONTAINING ONE OR MORE ORGANOSULFUR COMPOUNDS USING AN INTEGRATED COMPUTATIONAL ELEMENT

(71) Applicant: Halliburton Energy Services, Inc., Houston, TX (US)

(72) Inventors: Christopher Michael Jones, Houston, TX (US); Michael Pelletier, Houston, TX (US); Robert P. Freese, Pittsboro, NC (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/007,983

(22) PCT Filed: Nov. 29, 2012

(86) PCT No.: PCT/US2012/066934
§ 371 (c)(1),
(2) Date: Sep. 27, 2013

(87) PCT Pub. No.: WO2014/084822
PCT Pub. Date: Jun. 5, 2014

(65) Prior Publication Data
US 2014/0158876 A1    Jun. 12, 2014

(51) Int. Cl.
*G01V 5/00* (2006.01)
*E21B 44/00* (2006.01)
*E21B 37/06* (2006.01)
*E21B 41/02* (2006.01)
*E21B 43/16* (2006.01)
*G01N 27/72* (2006.01)

(52) U.S. Cl.
CPC ............... *E21B 44/00* (2013.01); *E21B 37/06* (2013.01); *E21B 41/02* (2013.01); *E21B 43/16* (2013.01); *G01N 27/72* (2013.01)

(58) Field of Classification Search
CPC ...................................................... G01N 23/02
USPC ........................................................ 250/253
See application file for complete search history.

(56) References Cited

U.S. PATENT DOCUMENTS

| 6,198,531 B1 | 3/2001 | Myrick et al. |
| 6,529,276 B1 | 3/2003 | Myrick |

(Continued)

FOREIGN PATENT DOCUMENTS

| JP | 2008116240 A | * | 5/2008 |
| WO | 2014084822 A1 | | 6/2014 |

OTHER PUBLICATIONS

International Search Report and Written Opinion for PCT/US2012/66934 dated May 27, 2013.

*Primary Examiner* — Kiho Kim
(74) *Attorney, Agent, or Firm* — McDermott Will & Emery LLP; Benjamin Fite

(57) ABSTRACT

The presence of organosulfur compounds in a substance may make analyses of the substance difficult, particularly in the presence of interfering compounds. Methods for analyzing a substance may comprise: providing a substance comprising an organosulfur compound; optically interacting electromagnetic radiation with the substance and an integrated computational element; and analyzing for the organosulfur compound in the substance using the integrated computational element.

24 Claims, 3 Drawing Sheets

(56) References Cited

U.S. PATENT DOCUMENTS

| | | |
|---|---|---|
| 6,670,605 B1 | 12/2003 | Storm, Jr. et al. |
| 7,123,844 B2 | 10/2006 | Myrick |
| 7,458,257 B2 | 12/2008 | Pop et al. |
| 7,733,490 B2 | 6/2010 | Goodwin et al. |
| 7,834,999 B2 | 11/2010 | Myrick et al. |
| 7,911,605 B2 | 3/2011 | Myrick et al. |
| 7,920,258 B2 | 4/2011 | Myrick et al. |
| 8,068,226 B2 | 11/2011 | Csutak |
| 2003/0134426 A1* | 7/2003 | Jiang et al. ............... 436/121 |
| 2004/0043501 A1 | 3/2004 | Means et al. |
| 2008/0149325 A1* | 6/2008 | Crawford .................... 166/68 |
| 2008/0253228 A1* | 10/2008 | Camwell et al. ............ 367/82 |
| 2009/0073433 A1 | 3/2009 | Myrick et al. |
| 2009/0219538 A1 | 9/2009 | Myrick et al. |
| 2009/0219539 A1 | 9/2009 | Myrick et al. |
| 2010/0091288 A1 | 4/2010 | DiFoggio et al. |
| 2010/0181471 A1 | 7/2010 | Pop et al. |
| 2013/0031970 A1 | 2/2013 | Freese et al. |
| 2013/0031971 A1 | 2/2013 | Freese et al. |
| 2013/0031972 A1 | 2/2013 | Freese et al. |
| 2013/0032333 A1 | 2/2013 | Freese et al. |
| 2013/0032334 A1 | 2/2013 | Freese et al. |
| 2013/0032340 A1 | 2/2013 | Freese et al. |
| 2013/0032344 A1 | 2/2013 | Freese et al. |
| 2013/0032345 A1 | 2/2013 | Freese et al. |
| 2013/0032545 A1 | 2/2013 | Freese et al. |

* cited by examiner

METHODS FOR ANALYZING SUBSTANCES CONTAINING ONE OR MORE ORGANOSULFUR COMPOUNDS USING AN INTEGRATED COMPUTATIONAL ELEMENT

BACKGROUND

The present invention generally relates to methods for analyzing organosulfur compounds and organosulfur compound-containing substances, and, more particularly, to methods for analyzing organosulfur compounds and organosulfur compound-containing substances using optical measurement techniques, optionally in the presence of one or more interfering compounds.

Hydrogen sulfide ($H_2S$) is a colorless and exceedingly poisonous gas that, in small quantities, has a foul odor of rotten eggs. In larger quantities, hydrogen sulfide dulls the olfactory senses and is essentially odorless. The latter represents an extremely hazardous situation, as serious injury or death may occur without one even being aware that they are being exposed to a dangerous substance. Common sources of hydrogen sulfide in the environment include, for example, metabolic waste products of anaerobic bacteria, volcanic eruptions, and natural gas emissions.

In the environment, organosulfur compounds frequently occur in concert with hydrogen sulfide. Many organosulfur compounds, particularly mercaptans (also known as thiols), also have a foul odor that is not greatly different than that of small quantities of hydrogen sulfide. Although some mercaptans and other organosulfur compounds may be toxic, they are generally much less so than hydrogen sulfide. As used herein, the term "mercaptan" refers to compounds having the formula RSH, where R comprises a carbon-containing group. Other organosulfur compounds include, for example, disulfides, sulfoxides, sulfones, sulfate esters, sulfonic acids, sulfonate esters, sulfinic acids, sulfinate esters, thiophenes, condensed thiophenes, combinations thereof, and the like. Hydrogen sulfide and mercaptans, in particular, can oftentimes be difficult to distinguish from one another due to their similar chemical and spectroscopic properties.

Once the presence of hydrogen sulfide and/or mercaptans has been established in a substance, profound implications can arise regarding the manner in which the substance is handled. In the health and safety regime, knowing whether an odiferous substance contains hydrogen sulfide, a mercaptan, or both, and the quantities of each can dictate appropriate handling techniques, disposal protocols, and any required personal protective equipment. From an operational standpoint, the acidity of hydrogen sulfide and mercaptans needs to be accounted for in engineering and process design due to the propensity of these compounds to promote corrosion and/or scaling on surfaces contacting the substance.

Despite the significant benefits that can be realized by analyzing for mercaptans and/or hydrogen sulfide in a substance, current techniques for doing so may be limited in their capabilities, particularly when both mercaptans and hydrogen sulfide are present. Non-spectroscopic chemical analyses may be complicated by difficult sample acquisition and/or preparation techniques and long analytical turn-around times, for example. Due to the similar chemical and spectral properties of hydrogen sulfide and mercaptans, spectroscopic analyses of hydrogen sulfide in the presence of mercaptans, or vice versa, may be complicated by significant spectral overlap, thereby making it difficult to distinguish between these compounds. Other spectral interferents such as carbon dioxide, for example, may also be problematic during spectroscopic analyses of hydrogen sulfide and/or mercaptans.

As noted above, the presence of hydrogen sulfide and/or mercaptans can have profound operational impacts in determining appropriate engineering solutions and process controls for an application. One industry in which hydrogen sulfide and/or mercaptans are frequently encountered is in the oilfield industry, where hydrogen sulfide and/or mercaptans are sometimes found downhole within a subterranean formation. Consequences of having mercaptans and/or hydrogen sulfide present during an oilfield operation may include corrosion of metal goods (e.g., tools, pipe, and the like) placed in the formation, formation of scale damage in the formation, or any combination thereof. In addition, the presence of excessive quantities of either type of compound, particularly hydrogen sulfide, may represent a health hazard for operational personnel. Depending on the quantity and location of hydrogen sulfide and/or mercaptans in the subterranean formation, different engineering solutions or process solutions may be needed to address their presence. For example, depending on the quantities of hydrogen sulfide and/or mercaptans present, it may sometimes be desirable to apply a corrosion-resistant coating to metal goods used downhole. In other cases, it may be more desirable to remediate the hydrogen sulfide and/or mercaptans directly, or, if possible, the source leading to their production.

Despite the advantages of analyzing for hydrogen sulfide and/or mercaptans during subterranean operations, state of the art techniques for doing so are surprisingly limited. Of the few techniques that are available, they may require difficult sampling, sometimes produce inaccurate results, and be too slow for real-time or near real-time process control. One technique that is commonly used for analyzing hydrogen sulfide and/or mercaptans in subterranean formations involves collection of a downhole fluid sample in a pressurized container for subsequent laboratory analysis. However, this technique can be prone to underestimation of the true quantities of these compounds due to their reaction with the container used for collection. Further, as noted previously, it may be difficult to analyze for these compounds in the presence of one another or in the presence of other interferents. Another technique that may be used to indirectly analyze for hydrogen sulfide and/or mercaptans in a subterranean formation involves a downhole metallic coupon test. Such tests, which measure corrosion, are slow, unable to distinguish between hydrogen sulfide and mercaptans, and of limited ability to determine the locale of hydrogen sulfide and/or mercaptans in the subterranean formation.

In addition to detecting and analyzing for hydrogen sulfide and/or mercaptans while conducting downhole operations, it can also be desirable to analyze for these substances once a produced fluid (e.g., oil or natural gas) has been sent for refining. If excessive quantities of one or both of these compounds are present, additional refining steps or alterations to the refining process may be needed to produce a refined fluid product having desired qualities. For example, hydrogen sulfide and mercaptans may poison catalysts used in conjunction with the refining process, and it may be desirable to decrease amounts of these compounds to levels that are more satisfactory to conduct the refining. Likewise, high levels of benzothiophenes in a produced fluid, for example, may lead to a refined product having sulfur levels that are too high to meet current environmental standards. If hydrogen sulfide, mercaptans, and/or other organosulfur compound levels in a subterranean formation are too excessive, it may not be economically feasible to refine a fluid produced therefrom, even if appropriate engineering solutions and process controls are undertaken during drilling and production. Thus, a decision may sometimes be made not to produce a subterranean formation based upon the formation's hydrogen sulfide and/or mercaptans content. In the event that higher than expected hydrogen sulfide and/or mercaptan levels are encountered once a wellbore has been placed into production, costly re-engineering and redesign may be needed to safely and effectively produce the formation. In view of the foregoing, the ability to accurately and rapidly determine the hydrogen sulfide and/or mercaptans content of a subterranean formation may be desirable.

SUMMARY OF THE INVENTION

The present invention generally relates to methods for analyzing organosulfur compounds and organosulfur compound-containing substances, and, more particularly, to methods for analyzing organosulfur compounds and organosulfur compound-containing substances using optical measurement techniques, optionally in the presence of one or more interfering compounds.

In some embodiments, the present invention provides methods comprising: providing a substance comprising an organosulfur compound; optically interacting electromagnetic radiation with the substance and an integrated computational element; and analyzing for the organosulfur compound in the substance using the integrated computational element.

In some embodiments, the present invention provides methods comprising: providing a substance comprising an organosulfur compound and hydrogen sulfide; optically interacting electromagnetic radiation with the substance and an integrated computational element; and analyzing for the organosulfur compound, the hydrogen sulfide, or any combination thereof in the substance using the integrated computational element.

In some embodiments, the present invention provides methods comprising: providing a fluid in a subterranean formation, the fluid comprising an organosulfur compound, or an organosulfur compound and hydrogen sulfide; optically interacting electromagnetic radiation with the substance and an integrated computational element; and determining an amount of the organosulfur compound, the hydrogen sulfide, or any combination thereof in the subterranean formation using the integrated computational element.

The features and advantages of the present invention will be readily apparent to one having ordinary skill in the art upon a reading of the description of the preferred embodiments that follows.

BRIEF DESCRIPTION OF THE DRAWINGS

The following figures are included to illustrate certain aspects of the present invention, and should not be viewed as exclusive embodiments. The subject matter disclosed is capable of considerable modifications, alterations, combinations, and equivalents in form and function, as will occur to those having ordinary skill in the art and the benefit of this disclosure.

DETAILED DESCRIPTION

Figure 1:
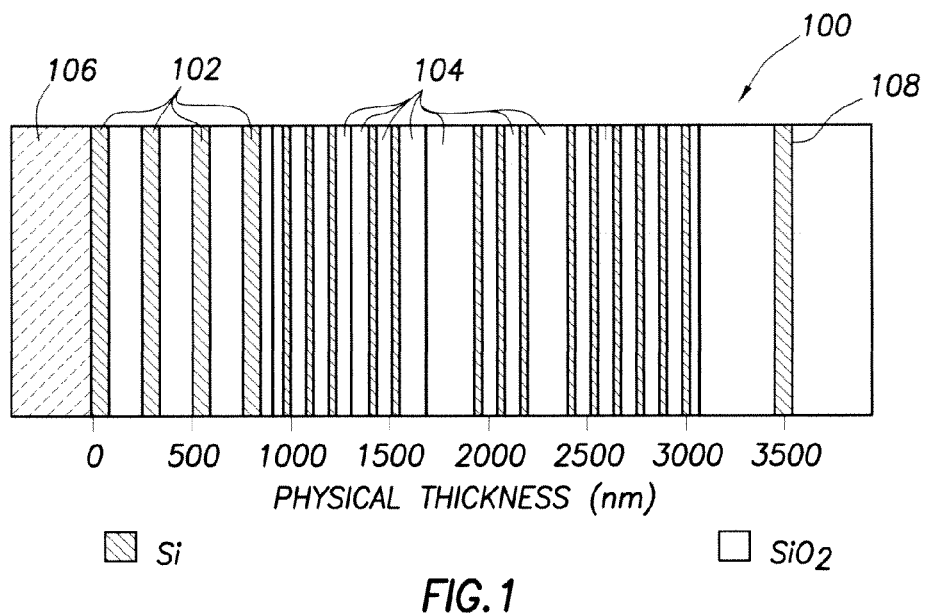
FIG. 1 shows a schematic of an illustrative integrated computational element (ICE).

The present invention generally relates to methods for analyzing organosulfur compounds and organosulfur compound-containing substances, and, more particularly, to methods for analyzing organosulfur compounds and organosulfur compound-containing substances using optical measurement techniques, optionally in the presence of one or more interfering compounds.

As described above, spectroscopic analyses of hydrogen sulfide and mercaptans in the presence of one another may be fraught with difficulties. Not only are such spectroscopic analyses complicated, but conventional spectroscopic instruments are generally unsuitable for being deployed in field or process environments. The foregoing problems may present particular difficulties in analyzing for these compounds in oilfield operations. Fluids removed from their subterranean environment may exhibit different properties than they do downhole, and analyses of hydrogen sulfide and/or mercaptans are no different in this regard. On the other hand, the delicate nature of conventional spectroscopic instruments may make them unsuitable for being placed in a subterranean formation for direct analyses downhole.

Despite the difficulties that can be encountered when analyzing for hydrogen sulfide and mercaptans, particularly in the presence of one another, significant benefits can be realized in doing so, especially by the techniques described herein. Moreover, the techniques described herein for analyzing these compounds may be particularly well suited for field and process environments, including downhole deployment within a subterranean formation. More specifically, the techniques described herein utilize optical computing devices containing one or more integrated computational elements (ICE) in conjunction with analyzing for mercaptans, mercaptans in the presence of hydrogen sulfide, hydrogen sulfide in the presence of mercaptans, or any combination thereof. Each integrated computational element within an optical computing device can be specifically configured to analyze for a constituent of interest in a sample, even when complex mixtures of constituents are present in a substance. Accordingly, depending on the type of analysis being conducted, the optical computing devices described herein may comprise at least an integrated computational element configured to analyze for an organosulfur compound, particularly a mercaptan or a combination of mercaptans, an integrated computational element configured to analyze for hydrogen sulfide, or any combination thereof. In some embodiments, the integrated computational element may be configured to analyze for a mixture of mercaptans without reference to the identity of the individual mercaptans therein. That is, in some embodiments, the integrated computational element may be configured to analyze for total mercaptans content. In other embodiments, the integrated computational element may be configured to analyze for a specific mercaptan, or multiple integrated computational elements may be present that are configured to analyze for specific mercaptans.

The theory behind optical computing and a description of some conventional optical computing devices are provided in more detail in the following commonly owned United States patents and United States patent application Publications, each of which is incorporated herein by reference in its entirety: U.S. Pat. Nos. 6,198,531; 6,529,276; 7,123,844; 7,834,999; 7,911,605; 7,920,258; 2009/0219538; 2009/0219539; and 2009/0073433. Accordingly, the theory behind optical computing will not be discussed in any extensive detail herein unless needed to better describe one or more embodiments of the present disclosure. Unlike conventional spectroscopic instruments, which produce a spectrum needing further interpretation to obtain a result, the ultimate output of optical computing devices is a real number that can be correlated in some manner with a concentration or characteristic of a sample. For example, in the embodiments described herein, the optical computing device may output a real number that may be correlated with an amount of one or more mercaptans, hydrogen sulfide, or any combination thereof in a sample. The operational simplicity of optical computing devices allows them to rapidly output a result, in real-time or near real-time, in some embodiments.

In addition, significant benefits can sometimes be realized by combining the outputs of two or more integrated computational elements with one another when analyzing for a single constituent or characteristic of interest. Specifically, in some instances, significantly increased detection accuracy may be realized. Techniques for combining the output of two or more integrated computational elements are described in commonly owned U.S. patent application Ser. Nos. 13/456, 255; 13/456,264; 13/456,283; 13/456,302; 13/456,327; 13/456,350; 13/456,379; 13/456,405; and 13/456,443, each filed on Apr. 26, 2012 and incorporated herein by reference in its entirety. Any of the techniques described herein may be carried out by combining the outputs of two or more integrated computational elements with one another. The integrated computational elements whose outputs are being combined may be associated or disassociated with the constituent or characteristic, display a positive or negative response when analyzing the constituent or characteristic, or any combination thereof.

As alluded to above, the operational simplicity of optical computing devices makes them rugged and well suited for field or process environments, including deployment within a subterranean formation. Uses of conventional optical computing devices for the analysis of fluids and other substances commonly encountered in the oil and gas industry, including while deployed within a subterranean formation, are described in commonly owned U.S. patent application Ser. Nos. 13/198,915, 13/198,950, 13/198,972, 13/204,005, 13/204,046, 13/204,123, 13/204,165, 13/204,213, and 13/204,294, each filed on Aug. 5, 2011 and incorporated herein by reference in its entirety.

The present inventors recognized that optical computing devices could advantageously be used to analyze for mercaptans and other organosulfur compounds to address current difficulties associated with their analyses, including those noted above. Further, the inventors recognized that these analyses could be conducted in the presence of hydrogen sulfide and other spectral interferents, such as carbon dioxide, for example, due to the specificity with which integrated computational elements may be configured. Moreover, the inventors recognized that using optical computing devices for these types of analyses would allow the analyses to take place in field and process environments, if desired, including within a subterranean formation, thereby addressing the sampling difficulties noted above. Finally, the rapid response times offered by optical computing devices may make them amenable to real-time or near real-time process control and monitoring.

From an operational standpoint, the techniques described herein may be particularly advantageous, since they may allow suitable engineering controls and process design to be implemented in processes once the presence of mercaptans and other organosulfur compounds, hydrogen sulfide, or any combination thereof has been confirmed. For example, employing the techniques described herein during subterranean operations may allow suitable materials to be chosen for use in conjunction with completing and producing a fluid from a subterranean formation, or for designing a treatment to be used in the subterranean formation. Moreover, the techniques described herein may provide guidance regarding appropriate refining techniques for a produced fluid as well as offering significant safety advantages for operational personnel.

In addition to the foregoing advantages, deploying one or more integrated computational elements downhole or in optical communication with the downhole environment may allow real-time or near real-time process control of a subterranean operation to take place. Specifically, if excessive quantities of hydrogen sulfide and/or mercaptans are detected using the integrated computational element(s), proactive steps may be taken to correct or otherwise address the out-of-range condition. For example, in some embodiments, a corrosion inhibitor, a scale inhibitor, a bacterial treatment (e.g., a bactericide or UV-light treatment), or any combination thereof may be introduced to the subterranean formation in order to mitigate the effects of the hydrogen sulfide and/or mercaptans therein. In other embodiments, a substance may be introduced to the subterranean formation that reacts with the hydrogen sulfide and/or mercaptans, where the hydrogen sulfide and/or mercaptans are less detrimental after reacting, in order to maintain process control. Moreover, detection and analysis of hydrogen sulfide and/or mercaptans within a subterranean formation using an optical computing device may serve as an alarm condition for operational personnel, thereby allowing appropriate safety measures to be taken, even if corrective actions within the subterranean formation cannot be taken at the time of detection. For example, detection of a rapid downhole increase in hydrogen sulfide and/or mercaptans may allow at least some time to prepare for the arrival of the hydrogen sulfide and/or mercaptans on the surface, to shut in the wellbore, and/or to evacuate the area surrounding the wellbore.

When hydrogen sulfide and/or mercaptans are suspected to be present in a subterranean formation, a corrosion inhibitor, a scale inhibitor, or any combination thereof may sometimes be introduced to the subterranean formation as a precautionary measure, instead of in response to the presence of these compounds. One disadvantage of this approach is that corrosion inhibitors and scale inhibitors can sometimes mask the presence of hydrogen sulfide and/or mercaptans, and a fluid may exhibit high levels of these compounds once produced to the surface. Thus, it can still be beneficial to analyze for hydrogen sulfide and/or mercaptans using an integrated computational element even if a corrosion inhibitor, a scale inhibitor, or any combination thereof is already being used as a precautionary measure. Moreover, the unnecessary use of corrosion inhibitors and scale inhibitors may significantly increase costs of conducting the subterranean operation. Use of an integrated computational element for monitoring subterranean operations in which hydrogen sulfide and/or mercaptans may be present may result in significant cost savings by limiting the unnecessary use of corrosion inhibitors, scale inhibitors, and other treatment chemicals.

Additional advantages of using an integrated computational element for analyzing mercaptans and/or hydrogen sulfide during subterranean operations may include determining a source of the sulfur comprising each type of compound, such as a biogenic source or another source. By knowing the total sulfur speciation, it may sometimes be possible to derive the conditions under which the sulfur-containing material was formed, as well as the type of source rock from which it is obtained. Through speciation of this type, it may also be possible to identify the formation source or location of the sulfur containing materials. Although such determinations may be made using conventional analyses, they may be facilitated considerably using an integrated computational element according to the embodiments described herein.

An integrated computational element may be used to provide distinct advantages when analyzing for hydrogen sulfide and/or mercaptans during the drilling stage of a subterranean operation. For example, if hydrogen sulfide and/or mercaptans are detected while drilling, it may sometimes be possible to bypass a region of the subterranean formation producing these materials in favor of another region where their production is lower or non-existent. Further, it may be advantageous to know when a reservoir of hydrogen sulfide and/or mercaptans has been encountered, since these materials may progress up the wellbore and pose a safety hazard for operational personnel. Similar to the description provided above, use of an integrated computational element to detect hydrogen sulfide and/or mercaptans during drilling may provide an early warning for operational personnel and allow appropriate action to be taken. For example, if an approaching influx of hydrogen sulfide and/or mercaptans is detected, it may be possible to shut in the wellbore, divert the hydrogen sulfide and/or mercaptans to a flare, change the drilling mud chemistry, implement self-contained or sourced breathing air sources for operational personnel, evacuate the surrounding area, or any combination thereof. Further, by being able to distinguish between hydrogen sulfide and mercaptans, the action being taken may be more appropriate for the true downhole condition being addressed, as compared to the action that might be taken based on the assumption that only hydrogen sulfide is being analyzed in a sample.

Although the foregoing discussion has primarily focused on the analysis of hydrogen sulfide and/or mercaptans in subterranean operations, it is to be recognized that the techniques described herein are equally applicable to any process in which it is desirable to detect these types of compounds. For example, in some embodiments, the techniques described herein may be used to analyze hydrogen sulfide and/or mercaptans in locations such as chemical plants, refineries, coking plants, paper mills, and water treatment facilities. In regard to water treatment facilities, in particular, the techniques described herein may be used to detect and analyze hydrogenسلف sulfide and/or mercaptans in the gas phase.

Moreover, although the foregoing discussion is primarily directed to the analysis of hydrogen sulfide and/or mercaptans and the advantages thereof, it is to be recognized that optical computing devices containing one or more integrated computational elements may be used to analyze for any type of organosulfur compound. In addition to mercaptans, illustrative organosulfur compounds that may be analyzed through modification of the techniques described herein include, for example, disulfides, sulfoxides, sulfones, sulfate esters, sulfonic acids, sulfonate esters, sulfinic acids, sulfinate esters, thiophenes, condensed thiophenes, combinations thereof, and the like. Oxidized variants of these organosulfur compounds may be analyzed as well. Specifically, the techniques described herein may be adapted for analysis of any of these types of compounds by using an appropriately configured integrated computational element.

As used herein, the term "fluid" refers to any substance that is capable of flowing, including particulate solids, liquids, gases, slurries, emulsions, powders, muds, glasses, any combination thereof, and the like. In some embodiments, the fluid can comprise an aqueous fluid, including water, mixtures of water and water-miscible fluids, brine, and the like. In some embodiments, the fluid can comprise a non-aqueous fluid, including organic compounds (i.e., hydrocarbons, oil, a refined component of oil, petrochemical products, and the like). In some embodiments, the fluid can be a treatment fluid or a formation fluid.

As used herein, the term "formation fluid" refers to a fluid that natively occurs within a subterranean formation.

As used herein, the term "treatment fluid" refers to a fluid that is placed in a location (e.g., a subterranean formation or a pipeline) in order to perform a desired function. Treatment fluids can be used in a variety of subterranean operations, including, but not limited to, drilling operations, production treatments, stimulation treatments, remedial treatments, fluid diversion operations, fracturing operations, secondary or tertiary enhanced oil recovery (EOR) operations, and the like. As used herein, the terms "treat," "treatment," "treating," and other grammatical equivalents thereof refer to any operation that uses a fluid in conjunction with performing a desired function and/or achieving a desired purpose. The terms "treat," "treatment," and "treating," as used herein, do not imply any particular action by the fluid or any particular component thereof unless otherwise specified. Treatment fluids for subterranean operations can include, for example, drilling fluids, fracturing fluids, acidizing fluids, conformance treatment fluids, damage control fluids, remediation fluids, scale removal and inhibition fluids, chemical floods, and the like.

As used herein, the terms "real-time" and "near real-time" refer to an output by an integrated computational element that is produced on substantially the same time scale as the optical interrogation of a substance with electromagnetic radiation. That is, a "real-time" or "near real-time" output does not take place offline after data acquisition and post-processing techniques. An output that is returned in "real-time" may be returned essentially instantaneously. A "near real-time" output may be returned after a brief delay, which may be associated with processing or data transmission time, or the like. It will be appreciated by one having ordinary skill in the art that the rate at which an output is received may be dependent upon the processing and data transmission rate.

As used herein, the term "substance" refers to a composition of matter containing one or more components therein.

As used herein, the term "electromagnetic radiation" refers to radio waves, microwave radiation, infrared and near-infrared radiation, visible light, ultraviolet radiation, X-ray radiation, and gamma ray radiation.

As used herein, the term "optically interact" and variations thereof refer to the reflection, transmission, scattering, diffraction, or absorption of electromagnetic radiation either on, through, or from one or more integrated computational elements. Accordingly, optically interacted electromagnetic radiation refers to electromagnetic radiation that has been reflected, transmitted, scattered, diffracted, absorbed, emitted, or re-radiated from a substance.

FIG. 1 shows a schematic of an illustrative integrated computational element (ICE) 100. As illustrated in FIG. 1, ICE 100 may include a plurality of alternating layers 102 and 104 of varying thicknesses disposed on optical substrate 106. In general, the materials forming layers 102 and 104 have indices of refraction that differ (i.e., one has a low index of refraction and the other has a high index of refraction), such as Si and $SiO_2$. Other suitable materials for layers 102 and 104 may include, but are not limited to, niobia and niobium, germanium and germania, MgF, and SiO. Additional pairs of materials having high and low indices of refraction can be envisioned by one having ordinary skill in the art, and the composition of layers 102 and 104 is not considered to be particularly limited. In some embodiments, the material within layers 102 and 104 can be doped, or two or more materials can be combined in a manner to achieve a desired optical response. In addition to solids, ICE 100 may also contain liquids (e.g., water) and/or gases, optionally in combination with solids, in order to produce a desired optical response. The material forming optical substrate 106 is not considered to be particularly limited and may comprise, for example, BK-7 optical glass, quartz, sapphire, silicon, germanium, zinc selenide, zinc sulfide, various polymers (e.g., polycarbonates, polymethylmethacrylate, polyvinylchloride, and the like), diamond, ceramics, and the like. Opposite to optical substrate 106, ICE 100 may include layer 108 that is generally exposed to the environment of the device or installation in which it is used.

The number, thickness, and spacing of layers 102 and 104 may be determined using a variety of approximation methods based upon a conventional spectroscopic measurement of a sample. These methods may include, for example, inverse Fourier transform (IFT) of the optical transmission spectrum and structuring ICE 100 as a physical representation of the IFT. The approximation methods convert the IFT into a structure based on known materials with constant refractive indices.

It should be understood that illustrative ICE 100 of FIG. 1 has been presented for purposes of illustration only. Thus, it is not implied that ICE 100 is predictive for any particular constituent or characteristic of a given fluid. Furthermore, it is to be understood that layers 102 and 104 are not necessarily drawn to scale and should therefore not be considered as limiting of the present disclosure. Moreover, one having ordinary skill in the art will readily recognize that the materials comprising layers 102 and 104 may vary depending on factors such as, for example, the types of substances being analyzed and the ability to accurately conduct their analysis, cost of goods, and/or chemical compatibility issues.

The weightings that the layers 102 and 104 of ICE 100 apply at each wavelength are set to the regression weightings described with respect to a known equation, or data, or spectral signature. Briefly, ICE 100 may be configured to perform the dot product of the input electromagnetic radiation into ICE 100 and produce a desired loaded regression vector represented by each layer 102 and 104 for each wavelength. As a result, the output electromagnetic radiation intensity of the ICE 100 may be correlated to a characteristic of a sample. For example, the output electromagnetic radiation intensity may be correlated to an amount of organosulfur compound, hydrogen sulfide, or any combination thereof that may be present. Further details regarding how ICE 100 is able to distinguish and process electromagnetic radiation related to the characteristic or analyte of interest are described in U.S. Pat. Nos. 6,198,531, 6,529,276, and 7,920,258, each of which was previously incorporated herein by reference.

It is to be recognized the embodiments herein may be practiced with various blocks, modules, elements, components, methods and algorithms, which can be implemented through using computer hardware, software and combinations thereof. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the spirit and scope of the embodiments expressly described.

Computer hardware used to implement the various illustrative blocks, modules, elements, components, methods and algorithms described herein can include a processor configured to execute one or more sequences of instructions, programming or code stored on a readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable PROM), registers, hard disks, removable disks, CD-ROMS, DVDs, or any other like suitable storage device.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, methods described herein may comprise: providing a substance comprising an organosulfur compound; optically interacting electromagnetic radiation with the substance and an integrated computational element; and analyzing for the organosulfur compound in the substance using the integrated computational element. In some embodiments, the organosulfur compound may comprise a mercaptan. In some embodiments, the substance may further comprise hydrogen sulfide.

In some embodiments, methods described herein may comprise: providing a substance comprising an organosulfur compound and hydrogen sulfide; optically interacting electromagnetic radiation with the substance and an integrated computational element; and analyzing for the organosulfur compound, the hydrogen sulfide, or any combination thereof in the substance using the integrated computational element. In some embodiments, the organosulfur compound may comprise a mercaptan.

In some embodiments, the methods may further comprise detecting the electromagnetic radiation that has optically interacted with the substance and the integrated computational element, and generating an output signal based on the detected electromagnetic radiation. In some embodiments, the output signal may provide an analysis of the organosulfur compound. In some or other embodiments, the output signal may provide an analysis of the organosulfur compound, the hydrogen sulfide, or any combination thereof. The selection of a suitable detector will depend, at least in part, upon the type of electromagnetic radiation that optically interacts with the integrated computational element and the substance. In this regard, suitable detectors for detecting particular types of electromagnetic radiation will be familiar to one having ordinary skill in the art. Moreover, suitable means for producing an output signal will also be familiar to one having ordinary skill in the art.

In some embodiments, the methods may comprise providing the electromagnetic radiation that optically interacts with the substance and the integrated computational element. In some embodiments, the electromagnetic radiation that optically interacts with the integrated computational element and the substance may be provided from an external source such as a lamp, a laser, a light-emitting diode (LED), a blackbody, and the like. In some embodiments, the external source may comprise a radio wave source, a microwave radiation source, an infrared radiation source, a near-infrared radiation source, a visible light source, an ultraviolet radiation source, an X-ray radiation source, a gamma ray radiation source, or any combination thereof. In other embodiments, the substance being analyzed or a location near the substance being analyzed may emit electromagnetic radiation through a chemiluminescence, physiluminescence, or like process. That is, the electromagnetic radiation may arise from the environment in which the substance is disposed. Accordingly, an external source of electromagnetic radiation need not necessarily be supplied to practice the techniques described herein.

In some embodiments, the electromagnetic radiation detected after optically interacting with the integrated computational element and the substance may lie in the near-infrared region of the electromagnetic spectrum. In some embodiments, the detected electromagnetic radiation may lie within a wavelength range of about 1000 nm to about 5000 nm, or a range of about 1000 nm to about 4000 nm, or a range of about 1000 nm to about 3000 nm. Particularly suitable wavelength ranges for mercaptans, other organosulfur compounds, and hydrogen sulfide may include, for example, a range of about 1500 nm to about 2000 nm, or a range of about 2000 nm to about 3000 nm, or a range of about 3500 nm to about 4500 nm. Other detected wavelength ranges are possible and include, for example, detection in the radio wave region, the microwave radiation region, the infrared radiation region, the visible light region, the ultraviolet radiation region, the X-ray radiation region, the gamma ray radiation region, or any combination thereof.

Substances containing an organosulfur compound that may be analyzed by the techniques described herein are not believed to be particularly limited. In some embodiments, the substance may comprise a solid phase. In some embodiments, the substance may comprise a fluid phase, which may comprise a liquid phase or a gas phase. It is to be recognized that, in some embodiments, phase mixtures may be present as well. For example, a liquid phase may be admixed within a continuous solid phase. Likewise, a liquid phase may be admixed within a continuous gas phase (e.g., as dispersed liquid droplets, such as a mist), or a gas phase may be admixed within a continuous liquid phase.

In some embodiments, analyzing for the organosulfur compound in the substance may comprise detecting the organosulfur compound. In some embodiments, analyzing for the organosulfur compound, the hydrogen sulfide, or any combination thereof in the substance may comprise detecting the organosulfur compound, the hydrogen sulfide, or any combination thereof. Detecting an organosulfur compound, hydrogen sulfide, or any combination thereof may, in some embodiments, comprise determining if the organosulfur compound, the hydrogen sulfide, or any combination thereof is present in the substance in an amount above the detection limit of the detector being used to receive electromagnetic radiation that has optically interacted with the substance and the integrated computational element. In some embodiments, the methods may comprise determining if the amount of the organosulfur compound, the hydrogen sulfide, or any combination thereof is above a fixed threshold quantity that is above the detection limit. In either case, detecting the organosulfur compound, the hydrogen sulfide, or any combination thereof may take place without further reference to the actual amounts of any of these compounds in the substance being analyzed. Such detection may be useful, for example, when it is simply desired to know if unacceptable levels of organosulfur compounds, hydrogen sulfide, or any combination thereof are present in a substance being analyzed. For example, detection without reference to quantity may be useful to trigger an alarm condition alerting personnel to a potential leak or chemical exposure. In some or other embodiments, detection without reference to quantity may be used to trigger a response to an out-of-range condition. For example, an out-of-range condition may be used to trigger an automated or manual response to the out-of-range condition.

In some embodiments, it may be desirable to determine an amount of the organosulfur compound, the hydrogen sulfide, or any combination thereof using the integrated computational element. Specifically, in some embodiments, the optical intensity of the electromagnetic radiation that has optically interacted with the substance and the integrated computational element may be correlated with the amount of the organosulfur compound, the hydrogen sulfide, or any combination thereof that is present. In some embodiments, the correlation may comprise a direct proportion. In other embodiments, the correlation may comprise an exponential correlation, a logarithmic correlation, a polynomial correlation, or any combination thereof. In some embodiments, the electromagnetic radiation that is received by the detector may produce an output signal in which the correlation is established.

In some embodiments, the methods described herein may comprise identifying the organosulfur compound, the hydrogen sulfide, or any combination thereof. For example, in some embodiments, the techniques described herein may comprise determining whether a substance contains a mercaptan, hydrogen sulfide, or any combination thereof. As described above, although mercaptans and hydrogen sulfide have similar chemical properties, an appropriate response to the presence of either type of compound may be considerably different. In more specific embodiments, the methods described herein may be used to identify particular organosulfur compounds, particularly mercaptans. For example, by employing an integrated computational element configured to detect a specific mercaptan, receipt of a detectable signal from an optical computing device employing such an integrated computational element may serve as an identification of the mercaptan.

In some embodiments, a plurality of integrated computational elements, each being configured for detecting a specific organosulfur compound, particularly a mercaptan, may be used to determine a distribution of organosulfur compounds. As used herein, the term "distribution of mercaptans" or, more generally, "distribution of organosulfur compounds" refers to a composition containing two or more mercaptans or organosulfur compounds and their relative quantities therein. Specifically, determining a distribution of mercaptans or other organosulfur compounds in a substance may comprise identifying specific mercaptans in a substance and the quantities present therein. When used in conjunction with analyzing a substance found in a subterranean formation, determining a distribution of mercaptans may provide useful information regarding the formation itself. In other embodiments, the integrated computational element may be configured to analyze for a first plurality of organosulfur compounds, but not be configured to analyze for a second plurality of organosulfur compounds. Thus, in some embodiments, a single integrated computational element may be used to identify whether certain organosulfur compounds are present while excluding others.

In some embodiments, analyzing for the organosulfur compound in accordance with the methods described herein may comprise detecting the organosulfur compound, determining an amount of the organosulfur compound, identifying the organosulfur compound, determining a distribution of organosulfur compounds, or any combination thereof. Moreover, in some embodiments, the methods may further comprise determining an amount of hydrogen sulfide present in the substance. In some embodiments, analyzing for the organosulfur compound, the hydrogen sulfide, or any combination thereof may comprise detecting the organosulfur compound, detecting the hydrogen sulfide, determining an amount of the organosulfur compound, determining an amount of the hydrogen sulfide, identifying the organosulfur compound, determining a distribution of organosulfur compounds, or any combination thereof.

Illustrative organosulfur compounds that may be analyzed or identified by the methods described herein include, without limitation, mercaptans disulfides, sulfoxides, sulfones, sulfate esters, sulfonic acids, sulfonate esters, thiophenes, condensed thiophenes, combinations thereof, and the like. In more specific embodiments, mercaptans that may be analyzed or identified by the methods described herein include, for example, methanethiol, ethanethiol, 1-propanethiol, 2-propanethiol, 1-butanethiol, 2-butanethiol, isobutanethiol, t-butylthiol, and the like. Higher alkanethiols may be analyzed or identified as well such as, for example, pentanethiol isomers, hexanethiol isomers, heptanethiol isomers, octanethiol isomers, nonanethiol isomers, decanethiol isomers, and the like. Mixtures of any of the foregoing mercaptans may be analyzed and identified as well.

In some embodiments, the methods described herein may be used to analyze for an organosulfur compound in a subterranean formation. In some embodiments, the methods may be used to analyze for an organosulfur compound, hydrogen sulfide, or any combination thereof in a subterranean formation. In some embodiments, the integrated computational element(s) used in conjunction with the analyses may be deployed within the subterranean formation. When present within the subterranean formation, the integrated computational element(s) may be deployed in a fixed location (e.g., on tubulars, the wellbore casing, the wellstring, and the like) or they may be movable (e.g., through wireline deployment). In some embodiments, at least one integrated computational element may be placed substantially adjacent to each subterranean zone. In alternative embodiments, the integrated computational element(s) may be deployed external to the subterranean formation but remain in optical communication with the subterranean formation through use of an optical fiber or like electromagnetic radiation conduit. Through strategic deployment of the integrated computational element(s), either within or in optical communication with a subterranean formation, one may determine a location of the organosulfur compound, the hydrogen sulfide, or any combination thereof within the subterranean formation using the integrated computational element(s). For example, by placing at least one integrated computational element adjacent to or in optical communication with each subterranean zone, it may be possible to determine which zone is producing an organosulfur compound, hydrogen sulfide, or any combination thereof. By knowing the particular locations within a subterranean formation that are producing organosulfur compounds, hydrogen sulfide, or any combination thereof, one may take corrective action to respond to the presence of these compounds. Suitable types of corrective actions are discussed in more detail below.

Illustrative fluids in a subterranean formation that may be analyzed by the methods described herein include, for example, oil, liquid hydrocarbons, gaseous hydrocarbons, natural gas, reservoir brines, formation water, drilling muds, treatment fluids, any combination thereof, and the like. Analyses of native formation fluids such as oil, liquid and gaseous hydrocarbons, natural gas, formation water, and reservoir brines may, in some embodiments, be used to establish whether the formation is suitable for production. For example, analyses of a formation fluid may be used to establish whether organosulfur compound and/or hydrogen sulfide levels in the subterranean formation are too excessive to economically produce the formation or if appropriate engineering controls have been undertaken. Likewise, analyses of a drilling mud or treatment fluid may be used to determine whether organosulfur compound and/or hydrogen sulfide levels remain within acceptable limits once a wellbore has been drilled or is being drilled.

In some embodiments, it may be desirable to determine the biogenic source of the sulfur comprising the organosulfur compound, the hydrogen sulfide, or any combination thereof. Determination of the biogenic source of the sulfur may be used to determine, for example, whether the organosulfur compound and/or hydrogen sulfide is being produced by a biological source (e.g., sulfate-reducing bacteria) or is a natively present component of the subterranean formation (e.g., through geological emissions). In some embodiments, methods described herein may further comprise determining a biogenic source of the sulfur comprising the hydrogen sulfide, the organosulfur compound, or any combination thereof using the integrated computational element. Determination of the biogenic source of the sulfur may comprise identifying particular organosulfur compounds that may be linked to a specific biological source, identifying bacteria producing the organosulfur compounds, or any combination thereof using the integrated computational element. Determination of the biogenic source of the sulfur may assist in deciding how to best address the presence of the organosulfur compounds and/or hydrogen sulfide, or if they can even be effectively addressed.

In some embodiments, methods described herein may comprise providing a fluid in a subterranean formation, the fluid comprising an organosulfur compound, or an organosulfur compound and hydrogen sulfide; optically interacting electromagnetic radiation with the substance and an integrated computational element; and determining an amount of the organosulfur compound, the hydrogen sulfide, or any combination thereof in the subterranean formation using the integrated computational element.

Determination of an amount of the organosulfur compound and/or hydrogen sulfide may take place at any time within the subterranean formation. In some embodiments, the organosulfur compound and/or hydrogen sulfide may be determined while drilling the subterranean formation. In some embodiments, the organosulfur compound and/or hydrogen sulfide may be determined while completing the subterranean formation. In some embodiments, the organosulfur compound and/or hydrogen sulfide may be determined while remediating or treating the subterranean formation. In still other embodiments, the organosulfur compound and/or hydrogen sulfide may be determined while producing the subterranean formation.

If quantities of the organosulfur compound and/or hydrogen sulfide within the subterranean formation are within acceptable levels, it may not be necessary to take corrective action in the subterranean formation. However, in some embodiments, if quantities of the organosulfur compound and/or hydrogen sulfide are above acceptable limits, the methods may further comprise responding to the amount of the organosulfur compound, the hydrogen sulfide, or any combination thereof that has been determined in the subterranean formation using the integrated computational element. The response to excessive levels of the organosulfur compound and/or hydrogen sulfide may comprise decreasing the amount of either type of compound and/or otherwise mitigating their effects in the subterranean formation. For example, at the drilling stage, it may be possible to decrease the amount of the organosulfur compound and/or hydrogen sulfide encountered in the formation simply by changing the direction or orientation of drilling. By changing the direction of drilling, regions of the subterranean formation containing high concentrations of the organosulfur compound and/or hydrogen sulfide may be bypassed in favor of lower concentration regions in order to reach a pay zone of the formation.

In some cases, it may not be possible to effectively bypass a region of the subterranean formation that contains an organosulfur compound and/or hydrogen sulfide. If so, then it may be desirable to treat the subterranean formation to mitigate the presence of the organosulfur compound and/or hydrogen sulfide or to decrease quantities of the organosulfur compound and/or hydrogen sulfide located within the subterranean formation.

In some embodiments, responding to the amount of the organosulfur compound, the hydrogen sulfide, or any combination thereof may comprise adding a treatment to the subterranean formation so as to modify it, such that the organosulfur compound and/or hydrogen sulfide does not produce detrimental effects therein. For example, in some embodiments, treating the subterranean formation may comprise adding a corrosion inhibitor, a scale inhibitor, a bacterial treatment, a substance that reacts with the hydrogen sulfide or the organosulfur compound, or any combination thereof to the subterranean formation. Suitable corrosion inhibitors, scale inhibitors, and bacterial treatments will be familiar to one having ordinary skill in the art. Corrosion inhibitors may limit the surface erosion resulting from the acidity of mercaptans and/or hydrogen sulfide. Scale inhibitors may reduce the propensity of insoluble scale to form during a subterranean operation. Particularly, the scale inhibitor may comprise a scale inhibitor that decreases the propensity for sulfate scale to form in the presence of hydrogen sulfide. Bacterial treatments can include chemical treatments (e.g., bactericides), physical processes (e.g., ultraviolet light treatment), or any combination thereof. Such bacterial treatments may kill or inactivate sulfate-reducing bacteria that may comprise a source of the organosulfur compound and/or hydrogen sulfide in the subterranean formation.

In some embodiments, treating the subterranean formation may comprise adding a substance to the subterranean formation that reacts with the hydrogen sulfide, the organosulfur compound, or any combination thereof in order to decrease the detrimental effects of the hydrogen sulfide and/or organosulfur compound therein. For example, in some embodiments, an oxidizing agent may be added to the subterranean formation in order to convert mercaptans into organic disulfides, which may be much less problematic to deal with during production due to their much lower volatility. Likewise, addition of an oxidizing agent to the subterranean formation may also convert hydrogen sulfide to a higher sulfur oxidation state that is less problematic to deal with.

In some embodiments, sensors configured for detecting organosulfur compounds and/or hydrogen sulfide are described herein. In various embodiments, the sensors may comprise an optical computing device containing an integrated computational element, a detector configured to receive electromagnetic radiation that has optically interacted with a substance and the integrated computational element, and an output mechanism configured to produce an output received from the detector. Depending on the intended application for the sensors, the integrated computational element may be configured to analyze for an organosulfur compound (e.g., a mercaptan), hydrogen sulfide, or any combination thereof. In particular, the sensors may be configured to analyze for organosulfur compounds, organosulfur compounds in the presence of hydrogen sulfide, or hydrogen sulfide in the presence of organosulfur compounds. In further embodiments, the optical computing devices comprising the sensors may further comprise a source of electromagnetic radiation, including those noted above.

To facilitate a better understanding of the present invention, the following examples of preferred or representative embodiments are given. In no way should the following examples be read to limit, or to define, the scope of the invention.

EXAMPLES

Example 1

Detection of Hydrogen Sulfide in the Presence of Interfering Substances

Figure 2:
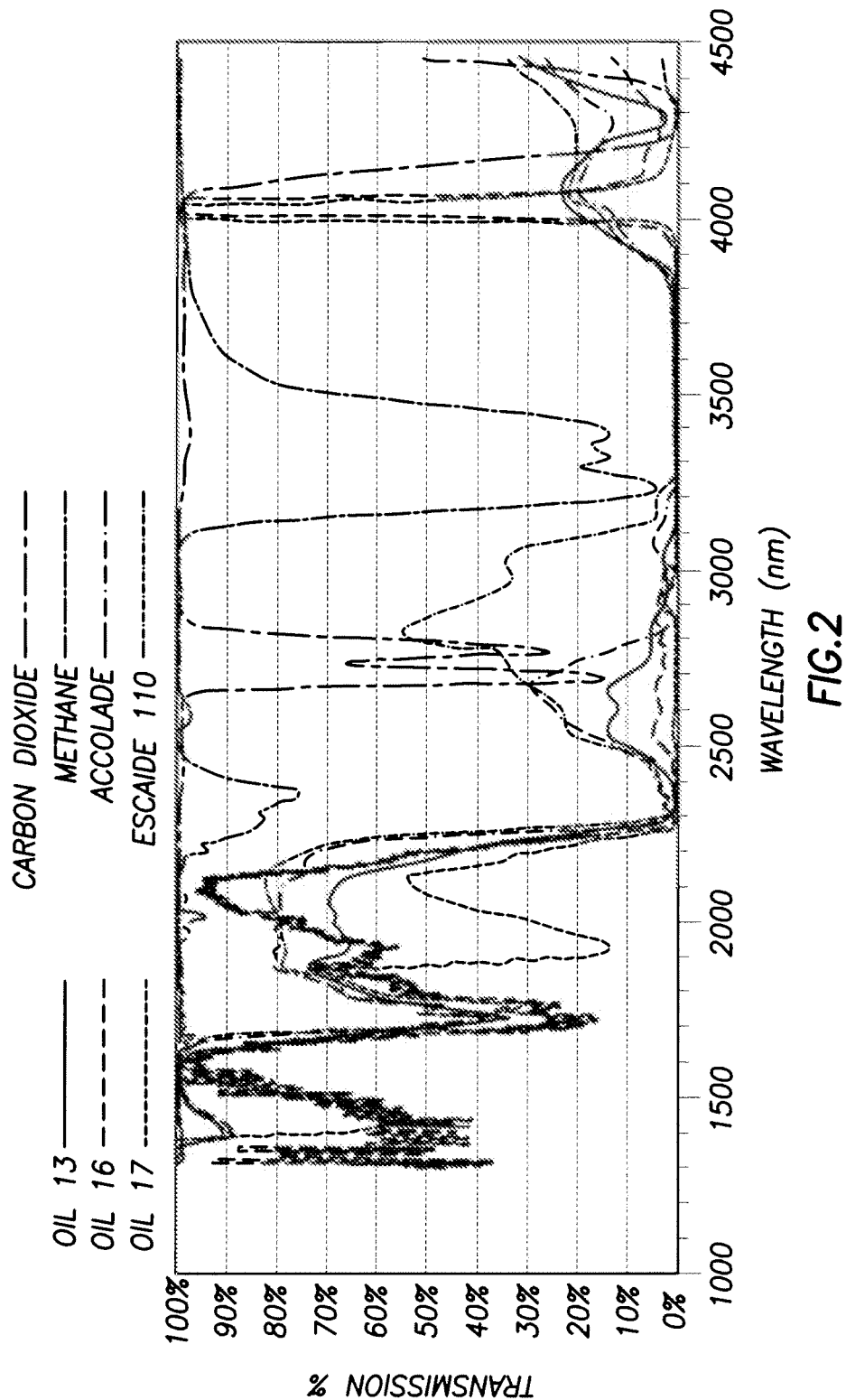
FIG. 2 shows illustrative near-infrared spectra for various oil samples and interfering substances.

Near-infrared spectra were obtained for three oil samples over a range of 1000 nm to 4500 nm. FIG. 2 shows illustrative near-infrared spectra for various oil samples and interfering substances. Oil 13 was obtained from the North Sea and contained about 10% asphaltenes and some mercaptans, but no $H_2S$. Oil 16 was obtained from the Gulf of Mexico and contained about 20% asphaltenes and some mercaptans, but no $H_2S$. Oil 17 was obtained from Saudi Arabia and contained 14% asphaltenes, some mercaptans, and about 25 ppm of $H_2S$. In FIG. 2, the near-infrared spectra of methane and carbon dioxide, which are common spectral interferents, are presented for comparison. In addition, the near-infrared spectra of ACCOLADE, a synthetic drilling mud available from Halliburton Energy Services, and ESCAIDE 110, an oil-based-drilling mud available from Halliburton Energy Services, are presented for comparison.

Figure 3A:
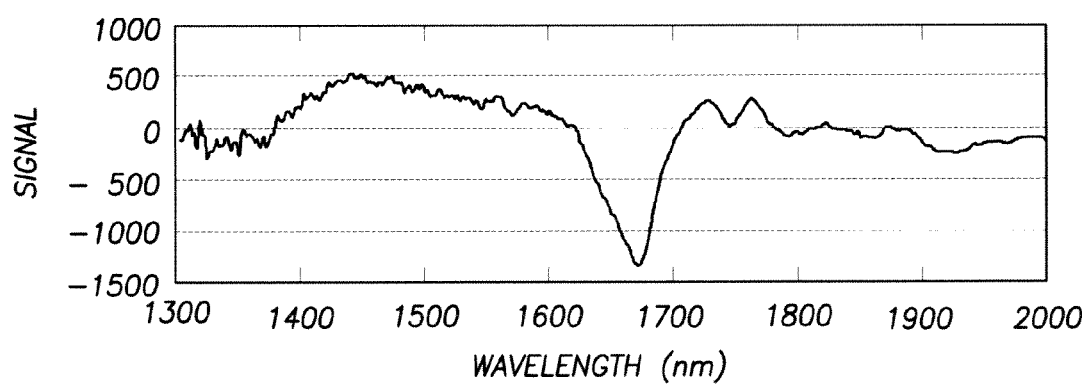
FIGS. 3A-3C show illustrative plots of the $H_2S$ regression vector over various wavelength ranges.
Figure 3B:
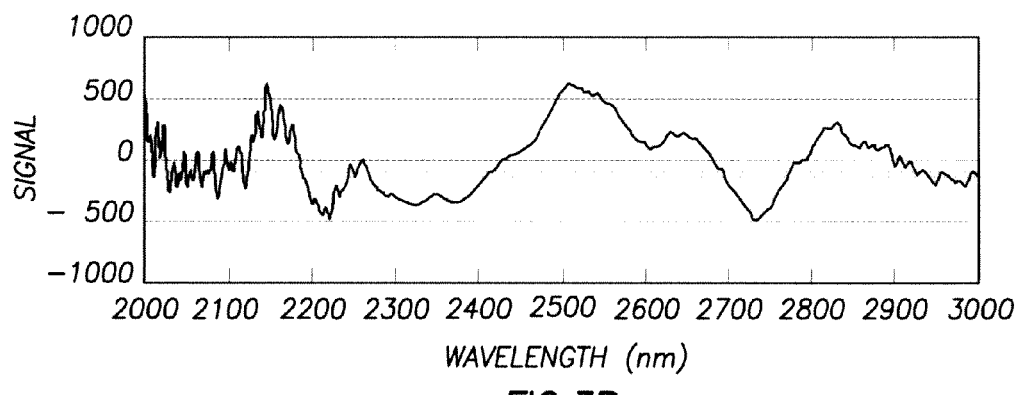
Figure 3C:
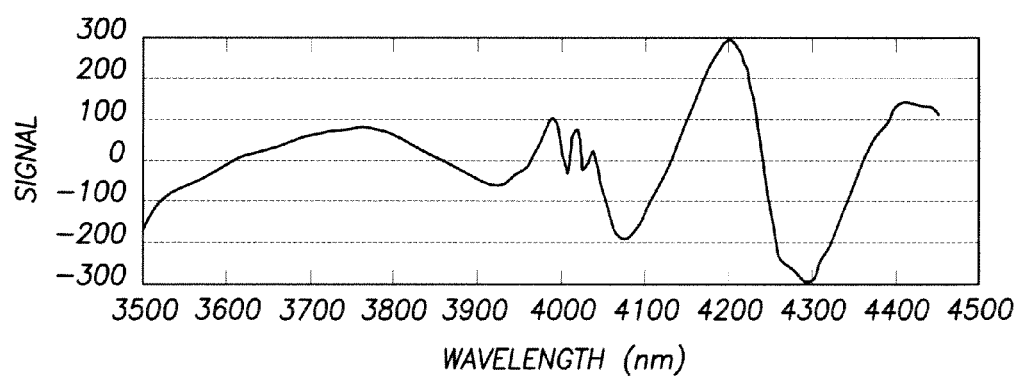

Multivariate regression analyses were performed on the spectra using partial least squares analyses in MATLAB software (Mathworks, Inc.). Using the partial least squares analyses, regression vectors for $H_2S$ were developed based upon 5 principal components. FIGS. 3A-3C show illustrative plots of the $H_2S$ regression vector over various wavelength ranges.

Using the regression vector in each region of interest, the hydrogen sulfide concentration was then measured for each sample using the dot product of the regression vector (i.e., C=I·R, where C is the concentration, I is the spectral intensity at the measured wavelength, and R is the regression vector at the measured wavelength). The hydrogen sulfide concentration for each sample was also determined using wet chemical and/or classical spectroscopic analyses for comparative purposes. The standard error of prediction for each sample was then determined by comparing the hydrogen sulfide concentration obtained using the regression vector to that obtained using wet chemical and/or classical spectroscopic analyses. Table 1 summarizes the standard error of prediction for the hydrogen sulfide concentration based upon the regression vectors (5 principal components) in each region of interest. In Table 1, the standard error of prediction within each region of interest is the average of that obtained for all samples.

TABLE 1

| Wavelength Range (nm) | Minimum $H_2S$ Concentration (ppm) | Maximum $H_2S$ Concentration (ppm) | Prediction Standard Deviation (ppm) | Standard Error (%) |
|---|---|---|---|---|
| 1305-4451 | 0 | 25 | 1.686 | 6.7 |
| 1305-2000 | 0 | 25 | 0.042 | 0.2 |
| 2000-3000 | 0 | 25 | 1.156 | 4.6 |
| 3500-4451 | 0 | 25 | 1.474 | 5.9 |

Thus, using the regression vectors, hydrogen sulfide was accurately determined in the parts per million and lower accuracy range, even in the presence of other organosulfur compounds (e.g., mercaptans) that are common interferents for these types of analyses.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. A method comprising:
    providing a substance comprising an organosulfur compound;
    optically interacting an incident electromagnetic radiation with the substance and an integrated computational element (ICE); and
    analyzing for the organosulfur compound in the substance using the ICE, wherein the ICE is configured so that an amplitude of the optically interacted radiation is indicative of a vector product between a spectral intensity of the incident electromagnetic radiation interacted with the substance and a regression vector for the organosulfur compound, and further wherein analyzing for the organosulfur compound comprises measuring the amplitude of the optically interacted radiation.

2. The method of claim 1, wherein analyzing for the organosulfur compound in the substance comprises detecting the organosulfur compound, determining an amount of the organosulfur compound, identifying the organosulfur compound, determining a distribution of organosulfur compounds, or any combination thereof.

3. The method of claim 1, wherein the organosulfur compound comprises a mercaptan.

4. The method of claim 1, further comprising:
    detecting the electromagnetic radiation that has optically interacted with the substance and the integrated computational element; and
    generating an output signal based on the detected electromagnetic radiation, the output signal providing an analysis of the organosulfur compound.

5. The method of claim 1, wherein the substance further comprises hydrogen sulfide.

6. The method of claim 1, wherein the substance comprises a fluid.

7. The method of claim 6, wherein the substance comprises a fluid selected from the group consisting of oil, a liquid hydrocarbon, a gaseous hydrocarbon, natural gas, a reservoir brine, a drilling mud, a treatment fluid, and any combination thereof.

8. The method of claim 1, wherein optically interacting electromagnetic radiation with the substance and the integrated computational element takes place in a subterranean formation.

9. The method of claim 8, further comprising:
    determining a location of the organosulfur compound in the subterranean formation using the integrated computational element.

10. A method comprising:
    providing a substance comprising an organosulfur compound and hydrogen sulfide;
    optically interacting an incident electromagnetic radiation with the substance and an integrated computational element (ICE); and
    analyzing for the organosulfur compound, the hydrogen sulfide, or any combination thereof in the substance using the ICE, wherein the ICE is configured so that an amplitude of the optically interacted radiation is indicative of a vector product between a spectral intensity of the incident electromagnetic radiation interacted with the substance and a regression vector for at least one of the organosulfur compound, the hydrogen sulfide or any combination thereof, and further wherein analyzing for the organosulfur compound, the hydrogen sulfide or any combination thereof comprises measuring the amplitude of the optically interacted radiation.

11. The method of claim 10, wherein analyzing for the organosulfur compound, the hydrogen sulfide, or any combination thereof in the substance comprises detecting the organosulfur compound, detecting the hydrogen sulfide, determining an amount of the organosulfur compound, determining an amount of the hydrogen sulfide, identifying the organosulfur compound, determining a distribution of organosulfur compounds, or any combination thereof.

12. The method of claim 10, wherein the organosulfur compound comprises a mercaptan.

13. The method of claim 10, further comprising:
detecting the electromagnetic radiation that has optically interacted with the substance and the integrated computational element; and
generating an output signal based on the detected electromagnetic radiation, the output signal providing an analysis of the organosulfur compound, the hydrogen sulfide, or any combination thereof.

14. The method of claim 10, wherein the substance comprises a fluid.

15. The method of claim 14, wherein the substance comprises a fluid selected from the group consisting of oil, a liquid hydrocarbon, a gaseous hydrocarbon, natural gas, a reservoir brine, a drilling mud, a treatment fluid, and any combination thereof.

16. The method of claim 15, further comprising:
determining a location of the organosulfur compound, the hydrogen sulfide, or any combination thereof in the subterranean formation using the integrated computational element.

17. The method of claim 10, wherein optically interacting electromagnetic radiation with the substance and the integrated computational element takes place in a subterranean formation.

18. The method of claim 10, further comprising:
determining a biogenic source of the sulfur comprising the hydrogen sulfide, the organosulfur compound, or any combination thereof using the integrated computational element.

19. A method comprising:
providing a fluid in a subterranean formation, the fluid comprising an organosulfur compound, or an organosulfur compound and hydrogen sulfide;
optically interacting an incident electromagnetic radiation with the substance and an integrated computational element (ICE); and
determining an amount of the organosulfur compound, the hydrogen sulfide, or any combination thereof in the subterranean formation using the ICE, wherein the ICE is configured so that an amplitude of the optically interacted radiation is indicative of a vector product between a spectral intensity of the incident electromagnetic radiation interacted with the substance and a regression vector for the organosulfur compound, and further wherein analyzing for the organosulfur compound comprises measuring the amplitude of the optically interacted radiation.

20. The method of claim 19, further comprising:
responding to the amount of the organosulfur compound, the hydrogen sulfide, or any combination thereof determined in the subterranean formation using the integrated computational element.

21. The method of claim 20, wherein responding comprises altering a direction or location of drilling in the subterranean formation.

22. The method of claim 20, wherein responding comprises treating the subterranean formation to decrease the amount of the organosulfur compound, the hydrogen sulfide, or any combination thereof that is present therein.

23. The method of claim 22, wherein treating the subterranean formation comprises adding a corrosion inhibitor, a scale inhibitor, a bacterial treatment, a substance that reacts with the hydrogen sulfide or the organosulfur compound, or any combination thereof to the subterranean formation.

24. The method of claim 19, wherein the organosulfur compound comprises a mercaptan.

* * * * *